US011253339B2

United States Patent
Bakry et al.

(10) Patent No.: US 11,253,339 B2
(45) Date of Patent: *Feb. 22, 2022

(54) METHOD FOR REMOVING METAL BRACKET FROM TEETH WITH A EUGENOL COMPOSITION

(71) Applicant: King Abdulaziz University, Jeddah (SA)

(72) Inventors: Ahmed Samir Ibrahim Bakry, Jeddah (SA); Mona Aly Abbassy, Jeddah (SA); Amal Linjawi, Jeddah (SA); Ali Habib Hassan, Jeddah (SA); Ahmed Fathy Hanafy, Jeddah (SA); Gihan Salah Labib, Jeddah (SA); Amal Mohammed S Abushal, Jeddah (SA)

(73) Assignee: King Abdulaziz University, Jeddah (SA)

(*) Notice: Subject to any disclaimer, the term of this patent is extended or adjusted under 35 U.S.C. 154(b) by 0 days.

This patent is subject to a terminal disclaimer.

(21) Appl. No.: 17/458,906

(22) Filed: Aug. 27, 2021

(65) Prior Publication Data

US 2021/0386521 A1 Dec. 16, 2021

Related U.S. Application Data

(60) Continuation of application No. 17/231,355, filed on Apr. 15, 2021, now Pat. No. 11,141,242, which is a division of application No. 16/952,556, filed on Nov. 19, 2020, which is a continuation of application No. 16/504,953, filed on Jul. 8, 2019, now Pat. No. 10,869,737, which is a division of application No. 15/782,328, filed on Oct. 12, 2017, now Pat. No. 10,426,576.

(51) Int. Cl.
*A61C 7/02* (2006.01)
*A61K 31/085* (2006.01)
*A61K 47/10* (2017.01)

(52) U.S. Cl.
CPC ............ *A61C 7/023* (2013.01); *A61K 31/085* (2013.01); *A61K 47/10* (2013.01)

(58) Field of Classification Search
CPC ....... A61C 7/023; A61K 47/10; A61K 31/085
USPC ........................................................ 433/216
See application file for complete search history.

(56) References Cited

U.S. PATENT DOCUMENTS

| | | | |
|---|---|---|---|
| 6,814,794 B2 * | 11/2004 | Allred | A61K 6/30 106/35 |
| 10,426,576 B2 * | 10/2019 | Bakry | A61C 7/023 |
| 11,141,242 B2 * | 10/2021 | Bakry | A61K 31/085 |
| 2004/0086830 A1 * | 5/2004 | Allred | A61K 6/889 433/89 |

(Continued)

FOREIGN PATENT DOCUMENTS

JP 2002-220313 A 8/2002

*Primary Examiner* — Matthew M Nelson
(74) *Attorney, Agent, or Firm* — Oblon, McClelland, Maier & Neustadt, L.L.P.

(57) ABSTRACT

The invention is directed to a composition that safely removes a cured dental cement or resin from metal brackets, metal braces, and enamel surfaces of teeth. It contains eugenol, isoeugenol, methyl-eugenol or an isomer thereof. A method for removing orthodontic fixtures adhered with a dental cement or resin to the enamel surfaces of teeth from these surfaces by contacting the dental cement or resin with a composition containing eugenol.

6 Claims, 4 Drawing Sheets

(56) References Cited

U.S. PATENT DOCUMENTS

| | | | |
|---|---|---|---|
| 2014/0370457 A1* | 12/2014 | Chun | A61C 1/07 |
| | | | 433/117 |
| 2015/0011452 A1* | 1/2015 | Guzman | A61K 6/887 |
| | | | 510/161 |
| 2016/0143978 A1 | 5/2016 | Potnis | |
| 2019/0110865 A1* | 4/2019 | Bakry | A61K 31/085 |
| 2019/0314432 A1 | 10/2019 | Garti | |

* cited by examiner

| Groups | N | Mean SBS (MPa) | Std. Deviation | Std. Error | 95% Confidence Interval | | Min. | Max. |
| --- | --- | --- | --- | --- | --- | --- | --- | --- |
| | | | | | Lower bound | Upper bound | | |
| Control | 15 | 6.68[a] | 1.73 | 0.61 | 5.23 | 8.12 | 4.11 | 8.56 |
| Eugenol 10min | 15 | 4.72[a] | 2.48 | 0.88 | 2.65 | 6.79 | 0.95 | 8.81 |
| Eugenol 24hrs | 15 | 2.29[a] | 0.69 | 0.61 | 1.71 | 2.87 | 1.01 | 3.30 |
| Sig. ($p<0.05$) | | | | | 0.005 | | | |

FIG. 4

| Groups | Adhesive Remnant Index (ARI) Scores | | | | Total |
|---|---|---|---|---|---|
| | 0 | 1 | 2 | 3 | |
| Control | 0 (0%) | 9 (62.5%) | 4 (25.0%) | 2 (12.5%) | 15 (100%) |
| Eugenol 10min | 0 (0%) | 11 (75.0%) | 2 (12.5%) | 2 (12.5%) | 15 (100%) |
| Eugenol 24hrs | 0 (0%) | 7 (50.0%) | 0 (0.0%) | 2 (50.0%) | 15 (100%) |
| Sig. ($p<0.05$) | | | 0.162 | | |

FIG. 5

METHOD FOR REMOVING METAL BRACKET FROM TEETH WITH A EUGENOL COMPOSITION

CROSS-REFERENCE TO RELATED APPLICATIONS

The present application is a Continuation of U.S. application Ser. No. 17/231,355, now allowed, having a filing date of Apr. 15, 2021 which is a Divisional of U.S. application Ser. No. 16/952,556, having a filing date of Nov. 19, 2020, which is a Continuation of U.S. application Ser. No. 16/504,953, now U.S. Pat. No. 10,869,737, having a filing date of Jul. 8, 2019 which is a Divisional of U.S. application Ser. No. 15/782,328, now U.S. Pat. No. 10,426,576, having a filing date of Oct. 12, 2017.

BACKGROUND

Field of the Invention

A method for removing a dental bracket, appliance, or prosthetic bound to a tooth or teeth with a dental adhesive or cement by contacting the dental adhesive or cement with an eugenol emulgel or eugenol in gel form. This method may be used to remove dental orthodontic brackets, fixed orthodontic appliances, fixed prosthetic elements, such as cemented laminates, veneers, fixed dental crowns, and fixed dental bridges bound to a tooth or to teeth.

Description of Related Art

The "background" description provided herein is for the purpose of generally presenting the context of the disclosure. Work of the presently named inventor(s), to the extent it is described in this background section, as well as aspects of the description which may not otherwise qualify as prior art at the time of filing, are neither expressly or impliedly admitted as prior art against the present invention.

Orthodontic fixed appliance treatment is a comprehensive procedure that starts with bonding brackets onto enamel surfaces of teeth and that ends with debonding of the brackets and removal of the brackets and residual bonding material from the enamel surfaces. Removal of the brackets is not difficult, but care must be taken during treatment with brackets to avoid breakage of the dental appliance containing the brackets and damage to tooth enamel. Brackets bonded directly to the teeth are removed by slightly deforming the base of the bracket. When the base of the bracket is squeezed, the bond releases and the bracket will come off. Usually, the separation occurs at the bracket-glue junction, leaving adhesive on the tooth surface. The orthodontist must then go back and remove the adhesive from each tooth. The process of removing brackets and the bonding cement or adhesive is relatively painless. After the braces have been removed, adhesive remaining on the teeth must be removed. This is usually done with a slow or high-speed dental hand piece that is the same type of instrument used by general dentists when they repair a cavity.

During debonding a dental practitioner will aim to limit this removal to the adhesive only leaving the enamel in its normal condition. However, conventional debonding procedures are risky as they can crack, flake, or fracture the enamel surface of a tooth as described by Pont H B, Ozcan M, Bagis B, Ren Y. "Loss of surface enamel after bracket debonding: an in-vivo and ex-vivo evaluation". Am J Orthod Dentofacial Orthop 2010;138:387 e1-389; and by Dumbryte I, Linkeviciene L, Malinauskas M, Linkevicius T, Peciuliene V, Tikuisis K. "Evaluation of enamel micro-cracks characteristics after removal of metal brackets in adult patients". Eur J Orthod 2011;35:317-322, each incorporated herein by reference in its entirety.

Another significant risk is a ceramic bracket fracture when conventional debonding procedures are used to debond ceramic brackets as described by Theodorakopoulou L P, Sadowsky P L, Jacobson A, Lacefield W. "Evaluation of the debonding characteristics of 2 ceramic brackets: an in vitro study". Am J Orthod Dentofacial Orthop 2004;125: 329-336; and by Fernandes T M F, Janson G, Somensi J, Pinzan A, Francisconi P A S, Sathler R, "Effects of modifying the bonding protocol on the shear bond strength of metallic and ceramic orthodontic brackets". Gen Dent 2012;6 0:51-55, each incorporated herein by reference in its entirety.

Many prior attempts have been made to solve these problems by reducing debonding forces to safely remove a dental appliance intact and to prevent damage to tooth enamel. However, while some of these attempts proved to be effective in reducing the debonding force, they resulted in further complications including pulpal damage caused by electrothermal devices or increases in adhesive remnants after treatment with laser devices as described by Jost-Brinkmann P-G, Radlanski R J, Ãrtun J, Loidl H. "Risk of pulp damage due to temperature increase during thermodebonding of ceramic brackets". Eur J Orthod 1997;19:623-628; Iijima M, Yasuda Y, Muguruma T, Mizoguchi I. "Effects of $CO_2$ laser debonding of a ceramic bracket on the mechanical properties of enamel". Angle Orthod 2010;80: 1029-1035; and by Ahrari F, Heravi F, Fekrazad R, Farzanegan F, Nakhaei S. "Does ultra-pulse $CO_2$ laser reduce the risk of enamel damage during debonding of ceramic brackets?" Lasers Med Sci 2012;27:567-574, each incorporated herein by reference in its entirety.

Orthodontic practitioners face a dilemma of using bonding procedures that produce strong and durable bonds that withstand forces applied during orthodontic treatment but which are difficult or unsafe to remove; and using less effective bonding procedures that are more easily debonded. Resolving this dilemma presents many challenges.

Composite resins are used in dentistry and orthodontia as bonding materials suitable for bonding to dental substrates, such as dentin, enamel, metal, ceramic, porcelain, and zirconia. They are used to bond orthodontic brackets to surfaces of teeth as well as to bond dental restorative materials such as glass ceramics, metal, composite resin, and zirconium oxide to teeth or other dental surfaces.

A dental composite resin may be a material that is light-cured, self-cured, and dual-cured. Generally a composite resin will contain a polymerizable monomer, a filler, and a polymerization initiator (e.g., a chemical catalyst or light). Composite resins are most widely used today as restorative materials for repairing fractures of teeth and dental caries or for orthodontic bonding. A cured composite resin is obtained after polymerization or curing of its ingredients and generally will have sufficient mechanical strength and hardness to serve as a substitute for natural teeth, provide wear resistance against occlusion of teeth in an oral cavity, have a surface smoothness and gloss, provide color matching with natural teeth, and provide translucency or transparency.

As a composite resin forming paste which has not yet been polymerized and cured, the composite resin should provide for ease of handling by dental or orthodontic clinicians and technicians, for example, it should exhibit proper fluidity and forming properties, adhere to surfaces to be bonded, but have substantially no adhesion to instruments used to apply it.

The micro-hardness and surface roughness of composite resins have been reported to be significantly affected by some chemical agents including topical fluoride agents (e.g., by Second Taste Gel which contains sodium fluoride), by coffee, and by low pH beverages as described by Yeh S-T, Wang H-T, Liao H-Y, Su S-L, Chang C-C, Kao H-C, et al., "The roughness, microhardness, and surface analysis of nanocomposites after application of topical fluoride gels". Dent Mater 2011;27:187-196; by Silva Jr J, Resin C, Microscope A F. "Analysis of Roughness and Surface Hardness of a Dental Composite using Atomic Force Microscopy and Microhardness Testing. Microsc Microanal", 2011;17:446-451; and by Hamouda I. M., "Effects of various beverages on hardness, roughness, and solubility of esthetic restorative materials". J Esthet Restor Dent 2011;23:315-322, each incorporated herein by reference in its entirety.

Limited studies have investigated the use of chemicals as debonding agents in orthodontic therapy. Larmour et al., in (1998), studied the effect of a marketed debonding agent that was based on peppermint oil (P-de-A®, Oradent, U.K.) on the debonding behavior of ceramic brackets and compared it to two well recognized softening agents; acetone and ethanol as described by Larmour C J, McCabe J F, Gordon P H. "An ex vivo investigation into the effects of chemical solvents on the debond behavior of ceramic orthodontic brackets". Br J Orthod 1998;25:35-40, incorporated herein by reference in its entirety. After application of peppermint oil for an hour, a decrease in the debonding strength and in the amount of adhesive remaining after debonding was reported. However, peppermint oil was not sufficient to significantly reduce the risk of ceramic bracket fracture.

In contrast to peppermint oil, eugenol is a phenylpropene, an allyl chain-substituted guaiacol and a member of the phenylpropanoids class of chemical compounds. It is a colorless to pale yellow, aromatic oily liquid extracted from certain essential oils especially from clove oil, nutmeg, cinnamon, basil and bay leaf. It is present in concentrations of 80-90% in clove bud oil and at 82-88% in clove leaf oil. The chemical structure of eugenol is shown below:

Eugenol is a phenol derivative that is used in combination with zinc oxide (ZnO) as a pulp capping agent, temporary cement and root canal filling cement. Eugenol-containing materials have several advantages as bases for restorations and eugenol is claimed to have sedative, anti-inflammatory, and analgesic effects on dental tissues as described by Hashimoto S, Maeda M, Yamakita J, Nakamura Y. "Effects of zinc oxide-eugenol on leucocyte number and lipoxygenase products in artificially inflamed rat dental pulp". Arch Oral Biol 1990;35:87-93; by Lee Y-Y, Hung S-L, Pai S-F, Lee Y-H, Yang S-F. "Eugenol suppressed the expression of lipopolysaccharide-induced proinflammatory mediators in human macrophages". J Endod 2007;33:698-702; by Li H Y, Lee B K, Kim J S, Jung S J, Oh S B. "Eugenol inhibits ATP-induced P2X currents in trigeminal ganglion neurons". Korean J Physiol Pharmacol 2008;12:315-321; and by Boeckh C, Schumacher E, Podbielski A, Haller B. "Antibacterial activity of restorative dental biomaterials in vitro". Caries Res 2001;36:101-107, each incorporated herein by reference in its entirety. Eugenol has been reported to stimulate the remineralization of carious dentin. Zinc oxide eugenol ("ZOE", which are often used as temporary fillings, is considered a better thermal insulator than most other lining materials as described by Little P A G, Wood D J, Bubb N L, Maskill S A, Mair L H, Youngson C C. "Thermal conductivity through various restorative lining materials". J Dent 2005;33:585-591, incorporated herein by reference in its entirety.

Eugenol is a chemical agent found in multiple dental materials including dental cements, filling materials, impression materials, endodontic sealers, periodontal dressing materials, dry socket dressings, an analgesics. Potnis, et al., U.S. Pat. No. 9,463,159 describes an oral gel containing eugenol, cooling agents, and camphor for relief of tooth pain. Prior compositions containing eugenol were used for pulp relief, usually applied after drilling a tooth cavity, and used as a temporary filling that set when it came into contact with saliva. Sometimes such compositions were used as temporary fillings for caries prior to removal of the caries. The contemporary use of eugenol for such purposes is now extremely rare because doctors commonly prescribe oral analgesics to relief pulpal pain and inflammation and because contemporary capping materials can be directly contacted with pulp to induce healing and reparative action in pulp cells. Thus, eugenol is not commonly used in modern dentistry.

The concentration of eugenol used in such materials is considered biologically inert, as there are only rare cases with adverse effects reported in the literature from its intra-oral application as described by Deshpande A, Verma S, Macwan C. "Allergic Reaction Associated with the use of Eugenol Containing Dental Cement in a Young Child". Austin J Dent 2014;1:1007, incorporated herein by reference in its entirety.

Studies of the effects of eugenol on the bond strength of resin bonding have produced contradictory findings. Although it has been claimed that eugenol-containing temporary cements compromise the resin-dentin bond strength of the permanent resin based cements, the overall effects were controversial and technique sensitive as described by Carvalho C N, Loguercio A D, Reis A. "Effect of ZOE Temporary Restoration on Resin-Dentin Bond Strength Using Different Adhesive Strategies". J Esthet Restor Dent 2007;19:144-152, incorporated herein by reference in its entirety.

Eugenol has shown to have an effect on composite resins and previous studies showed that the bond strength of both types of composite adhesives (etch-and-rinse or self-etch) was significantly affected after 24 h of contact with ZOE as described by Pinto K T, Stanislawczuk R, Loguercio A D, Grande R H M, Bauer J. "Effect of exposure time of zinc oxide eugenol restoration on microtensile bond strength of adhesives to dentin". Rev Port Estomatol Med Dent Cir Maxilofac 2014;55:83-88; and Nasreen F, Guptha A B S, Srinivasan R, Chandrappa M M, Bhandary S, Junjanna P. "An in vitro evaluation of effect of eugenol exposure time on the shear bond strength of two-step and one-step self-etching adhesives to dentin". J Consery Dent 2014;17:280-284, each incorporated herein by reference in its entirety. However, bond strength was re-established and became similar to their control groups after 7 days. These latter studies clarified that eugenol effects on composite restorations were temporary and limited to small areas.

Some attempts have been reported in the literature assessing the effect of eugenol and other solvents on the debonding behavior of orthodontic brackets. He, et al. reported that eugenol in IRM (Intermediate Restorative Materials) reduced the mechanical properties of composite resin within a limited range that does not affect the functionality of the restoration as described by He L-H, Purton D G, Swain M V. "A suitable base material for composite resin restorations: Zinc oxide eugenol". J Dent 2010;38:290-295, incorporated herein by reference in its entirety. However, the effects of eugenol on functional properties and debonding of composite resins is still under debate.

In view of the dilemma faced by orthodontic practitioners of providing a bonding resin or cement that is strong and durable, but which can be easily removed without substantial damage to enamel surfaces of teeth, the inventors investigated use of eugenol as a safe debonding agent. As shown herein, the inventors prepared eugenol in a gel form or as an "emulgel" that exhibited a surprising ability to reduce microhardness of orthodontic adhesive bonding resins and that facilitated the safe removal of orthodontic metal brackets as well as the removal of residual bonding resin for enamel surfaces of teeth.

BRIEF SUMMARY OF THE INVENTION

The invention is directed to a safe, non-toxic composition (e.g., emulgel) comprising eugenol or a derivative of eugenol in a gel or other viscous form suitable for application and adhesion to cured or hardened dental cement or bonding resins in the mouth. Once applied to a dental cement or resin, the composition reduces microhardness and permits its removal without substantial damage to the enamel surfaces of teeth or to the dental apparatus that is removed.

BRIEF DESCRIPTION OF THE DRAWINGS

FIGS. 1A and 1B.

FIG. 5 depicts Table 2. This table which describes the number and percentages of teeth under each ARI category for all the groups. Using Kruskal Wallis test, no significant difference was found at $p<0.05$. However, in combination with other data herein, these results show that at least similar amounts of bonding material were removed by debonding with a eugenol-containing emulgel according to the invention while rendering debonding safer due to decreases in Vickers hardness of dental cement or resin and debonding forces.

DETAILED DESCRIPTION OF THE INVENTION

As disclosed herein the inventors sought to improve the efficacy and safety of dental debonding procedures, such as those involving removal of metal brackets bound via a dental cement or dental resin to the enamel surfaces of teeth. Eugenol is conventionally used to make temporary dental cements, for example, in combination with zinc oxide and is also a component of clove oil. Thus, it is recognized as safe both as a food ingredient and in dental materials. However, eugenol is a liquid and quickly dissipates when placed in the mouth. Moreover, its capacity to reduce the hardness of cured dental cements and resins as well as to facilitate the removal of dental brackets from teeth had not been established. The inventors disclose herein a method for reducing the hardness of cured dental cements and resins and for more safely removing dental brackets and other dental appliances or prosthetics by application of a persistent form of eugenol. As disclosed herein, the inventors have produced eugenol in a gel form as an "emulgel" that when applied to cured dental cement or resins in the mouth prolongs the release of eugenol thus making the cured dental cement or resin less hard and easier and safer to remove.

A debonding composition according to the invention will contain eugenol in a form that permits prolonged contact between a dental cement or resin and the eugenol in the composition, for example, in a preferred form contains eugenol and one or more surfactants, cosurfactants, pH-adjusting agents, preservatives, or other ingredients.

Eugenol. Eugenol is phenylpropene, an allyl chain-substituted guaiacol and a member of the phenylpropanoids class of chemical compounds. Eugenol and/or its derivatives and isomers such as isoeugenol, methyl-eugenol or an isomer thereof may be employed in some embodiments of the invention. Eugenol is a liquid that quickly disperses when administered into the mouth. In contrast, the invention provides eugenol in a form, such as a gel, that once applied persists and releases eugenol over a period of time thus providing for continuing softening of dental cement or resin that fix metal bracket or other dental appliances or prosthetics to teeth. In preferred embodiments of the invention a debonding composition will be in the gel form containing eugenol in an effective amount which may range from about 0.5-25 wt % based on the weight of the debonding composition. The eugenol content range includes all subranges and intermediate values including 0.5, 1, 2, 3, 4, 5, 6, 7, 8, 9, 10, 12.5, 15, 17.5, 20, 22.5, 25, 30, 35, 40, 45, 50, 55, 60, 65, 70, 75, 80, 85, 90, 95 or <100%. In most embodiments, the content of eugenol will not exceed that necessary to maintain a composition in a stable, easily applicable gel form.

Effective amount. As used herein, the term "effective amount" means a quantity of eugenol required to reduce the Vickers hardness of a dental cement or resin, to reduce force needed to debond a metal bracket or other dental prosthetic from the surface of a tooth, or to reduce residual dental cement or resin on surfaces of teeth that remain after removal of a dental bracket or prosthetic.

Gel base. A gel base and its content of ingredients are selected to provide for sustained release of eugenol after application to a dental cement or resin. Gel bases include, but are not limited to, an anionic polymer, such as a polycarboxylate, poly(acrylic acid, which may be crosslinked, polyalkenyl ethers, divinyl glycol, 1:4 to 4:1 copolymers of maleic anhydride or maleic acid with another polymerizable ethylenically unsaturated monomer such as methyl vinyl ether/maleic anhydride (PVM/MA) copolymer. A gel base may be in free or salt form. In preferred embodiments of a debonding composition (e.g., emulgel) of the invention, the gel base may comprise a carbomer (e.g., Carbopol 934, Carbopol 940), hydroxy propyl methyl cellulose (e.g., HPMC K4M), polaxamer, carboxy methyl cellulose sodium or other gelling agents in an amount ranging from 0.5-10 wt %, which range includes all subranges and intermediate values including 0.5, 1, 2, 3, 4, 5, 6, 7, 8, 9, 10, 15, 20, 25, 30, 35, 40, 45, 50, 55, 60, 65, 70, 75, 80, 85, 90, or 95 wt %.

Surfactants. Include nonionic surfactants such as poloxamers, polysorbates, and mixtures thereof. In some preferred embodiments one or more surfactants such as a polysorbate (e.g., Tween 80/polysorbate 80, Tween 20/polysorbate 20), cremophore (e.g., Cremophore RH40) are incorporated in an amount ranging from 1 to 40 wt %, which range includes all subranges and intermediate values including about 1, 2, 3, 4, 5, 6, 7, 8, 9, 10, 15, 20, 25, 30, 35, 40, 45, 50, 55, 60, or 65 wt %.

Cosurfactants. In some preferred embodiments one or more co-surfactants such as polyethylene glycol, propylene glycol, glycerol are added in an amount ranging from 2.0-30 wt %, which range includes all subranges and intermediate values including about 2, 3, 4, 5, 6, 7, 8, 9, 10, 15, 20, 25 and 30 wt %.

pH-adjusting agents. A buffer or other pH adjusting agent such as sodium hydroxide or triethanol amine may be added in an amount sufficient to titrate the pH of the emulgel or other composition of the invention to fall within the range of about pH 4-8.0 and preferably within the range of about pH. 6.0-6.5. This range includes all subranges and intermediate values including 4, 4.5, 5.0, 5.5, 6.0, 6.5, 7.0, 7.5, and 8.0. pH may also be adjusted based on the oral pH of a subject. Saliva usually has a pH ranging from 6.2 to 7.6 and pH of a composition of the invention may be matched to that of the oral pH or to be about 0.25, 0.5, 0.75, or 1.0 pH units below or above it.

Preservatives. A debonding composition according to the invention may contain one or more preservatives to extend its useful life, prevent oxidation, or prevent microbial contamination. In some preferred embodiments one or more preservatives such as a paraben (e.g., methyl-paraben, propy-1-paraben, or butyl-paraben) are added in an amount ranging from 0.01 to 0.45 wt %, which range includes all subranges and intermediate values including at least about 0.01, 0.02, 0.03, 0.04, 0.05, 0.075, 0.1, 0.2, 0.25, 0.3, 0.4, and 0.45 wt. %.

Other components. Other ingredients such as at least one buffer or pH-adjusting agent (e.g., acidifier or basifier), sweetener, analgesic, cooling agent (e.g., menthol, camphor, peppermint oil), soothing agent (e.g., 2-ethoxylbenzoic acid, 2-methyl-4-methyphenol, tall oil, rosin or pine gum; $KNO_3$), anti-inflammatory agent, antibiotic, astringent, lubricants, electrolytes (e.g., sodium potassium, magnesium, calcium; chloride, fluoride, iodide, bicarbonate or phosphate) or solvent (e.g., DMSO) may optionally be incorporated into a eugenol-containing gel that is used for debonding. Particles, such as microparticles or nanoparticles, or liposomes, encapsulating or incorporating eugenol that is released over a preselected period of time such as those disclosed herein may also be incorporated into a gel or non-gel composition according to the invention. Such particles or liposomes may be produced by methods known in the art or those disclosed and incorporated by reference to Hudson, et al., U.S. Pat. No. 9,102,573, to Fountain, U.S. Pat. No. 9,364,434 or to Shefer, et al., U.S. Pat. No. 7,670,627. In some embodiments one or more of these other components are present, in others they are absent.

Eugenol-Containing Temporary Adhesives, Viscous Forms and Other Non-Gel Forms

Eugenol may also be compounded in a non-gel form that adheres or binds to dental cement or resin such as that fixing a metal brace to an enamel surface of a tooth. Like gel forms these are formulated to temporarily adhere and prolong the release of eugenol into a dental cement or resin. In some embodiments a composition according to the invention may be in a solid or semi-solid form, such as a hardened coating, paint, varnish, or putty out of which eugenol can leach, or in the form of an aerosol, vapor, gas, or ionized gas, such as an aerosol spray containing eugenol that is applied to, sprayed on, pressure-sprayed on, or pressurized into a hardened or cured dental cement or resin.

Units of weight. Unless otherwise specified, all percentages and amounts expressed herein and elsewhere in the specification refer to percentages by weight and the amounts given are based on the weight of the material and weight-percent (wt. %) is based on the amount of a material divided by the total weight of the debonding composition.

Viscosity. Viscosity of a liquid, semi-liquid or semi-solid composition of the invention can be measured in units of centipoise ("cP") or one millipascal-second (mPa·s). A composition according to the invention may be formulated at a viscosity sufficient to contact eugenol, isoeugenol, methyl-eugenol or an isomer thereof with a cured or hardened orthodontic or dental cement or resin for a time sufficient to reduce its Vickers hardness, for example, to reduce Vickers hardness to 90, 80, 70, 60, 50, 40, 30, 20, 10 or less. Preferably, such a composition will be in the form a gel or viscous liquid which can easily be applied to or contacted with dental cement or resin bound to teeth, orthodontic brackets, or other dental fixtures. Viscosity of a composition according to the invention generally range from 1,000 to 100,000,000 centipoise including all intermediate subranges and values such as at least 1,000, 5,000, 10,000, 50,000, 100,000, 500,000, 1,000,000, 5,000,000, 10,000,000, 50,000,000 and 100,000,000 centipoise (cP). Compounds having viscosities within this range include water (1 cP), blood or kerosene (10 cP), antifreeze or ethylene glycol (15 cP), motor oil SAE 10 or corn syrup (50-100 cP), motor oil SAE 30 or maple syrup (150-200 cP), motor oil SAE 60 or glycerin (1,000-2,000 cP), corn syrup or honey (2,000-3,000 cP), blackstrap molasses (5,000-10,000 cP), chocolate syrup (10,000-25,000 cP), ketchup or prepared mustard (50,000-70,000 cP), tomato paste or peanut butter (150,000-2,000,000 cP), shortening or lard (1,000,000-10,000,000 cP), caulking compound (5,000,000-10,000,000 cP) and window putty (100,000,000 cP). In some embodiments, the viscosity of a composition of the invention ranges from about 1,000 centipoise (cPs) to about 10,000,000 cPs, in other embodiments range from about 10,000 cP to about 1,000,000 cPs, and in other embodiments from 100,000 cPs to about 500,000 cPs. These ranges include all subranges and inter-mediate values. In other embodiments a eugenol-containing composition according to the invention may be in a liquid or semi-liquid forms, such as thin liquid (e.g., 1-15 cP), thick liquid (>15 cP), foam, gel, emulsion, ointment, salve, or paste. The rate of release of eugenol by an emulgel may be modulated by increasing or decreasing its concentration in the emulgel or by raising or lowering the viscosity of the emulgel.

Oral application. A gel containing eugenol or a eugenol composition in another viscous or other form that is capable of adhering around metal brackets or other dental appliances affixed to teeth with a bonding cement or resin may be applied by various known methods, for example, by application with a dental tool, syringe, brush or spray.

Such a eugenol-containing composition must be capable of continuously exposing the bonding cement or resin to the eugenol it contains for a period of time sufficient for significant dehardening of the cement or resin. For example, a eugenol-containing gel or other composition will be formulated so as to persist on or around the dental cement or resin and release eugenol into it for a period of time ranging from at least 5, 10, 15, 20, 30, or 60 mins, or for at least 1, 2, 3, 4, 5, 6, 7, 8, 9, 10, 12, 16, 20, 24 hours. In some cases, a eugenol-containing gel or other composition may be reapplied once or more than once at intervals, for example at intervals of 15, 30, or 60 mins, of 2, 4, 6, 8, or 12 hours.

In some embodiments, a composition of the invention may be applied under pressure or by impacting particles or droplets of the composition against dental cement or resin, in others it is applied under normal atmospheric pressure, for example, by painting or coating it on a dental cement or resin or by soaking a dental cement or resin in it. In other embodiments, a eugenol-containing composition may be formulated in a binary form comprising two or more liquids than when mixed form a solid cast around dental cement or resin on teeth or dental fixtures. However, preferably, a composition according to the invention will be in gel form, such as in an emulgel as disclosed herein.

In some embodiments, prior to application of a eugenol-containing composition, the surface containing the dental cement or resin may be brushed, buffed, polished, washed or etched to remove microbial or chemical coatings (such as biofilm or adherent proteins, carbohydrates or lipids).

Assessment of Debonding Strength. Debonding strength was assessed substantially according to a method described by Bishara et al. who developed a clinically representative method using debonding pliers mounted on the Instron Universal Machine. Bishara debonding force was described as being similar to the force applied during a diametral compression test for tension. The diametral compression test was considered as a way of indirectly measuring the tensile strength of a material that exhibited very limited plastic deformation such as ceramics, composites, and enamel. The debonding pliers were unique in that they applied the force at the bracket-adhesive interface on both sides of the bracket simultaneously as a bilateral load. Bishara further compared the differences between the actual forces generated during bracket removal in the clinical setting and the shear forces applied during laboratory testing for debonding ceramic brackets. Their results indicated that debonding with pliers required the application of 30% less force to the enamel surface than debonding with shear forces as tested in the laboratory.

There were no significant differences in the Adhesive Remnant Index (ARI) of the two groups, i.e. where the bond failures occurred in their study. Thus, Bishara suggested that applying the load to the two sides of the bracket increased the chances of starting a crack and propagating it in the brittle adhesive causing debonding to occur at a lower debonding force. Horiuchi et al, also adopted such method in assessing the bond strength.

In a previous study, a finite element analysis showed that the least amount of stress on enamel during debonding occurred when applying lateral rotation force on the bracket with a debonding plier as described by Holberg C, Winterhalder P, Holberg N, Wichelhaus A, Rudzki-Janson I. "Orthodontic bracket debonding: risk of enamel fracture". Clin Oral Investig 2014;18:327-334, incorporated herein by reference in its entirety. Lateral rotation was defined in Holberg et al. study as the pliers exerting force on the occlusal and gingival parts of the brackets and causing lateral rotation at debonding. The force of the pliers in the examples described herein was applied at the bracket-adhesive interface in an occluso-gingival direction (bilateral load). However, due to the thin bracket-adhesive interface, the slippage of the plier blades was common and a lateral rotation stress was mostly applied during debonding.

In the examples herein and as a referent resin, the inventors used a widely-used and copied resin cement: Trans Bond XT® manufactured by 3M company, which is incorporated by reference to http://_multimedia.3 m.com/mws/media/111911O/transbond-xt-light-cure-orthodontic-adhe-sive-ifu.pdf?&fn=TransbondXT_011-519-11_ML_1205.p (last accessed Aug. 28, 2017). A Trans Bond XT® product is also described by the 3M products on sale in 2016 or 2017 bearing this name and trademark. However, the method of the invention may be used to help remove other similar types of resin cements or other kinds of dental cements.

Fourier-transform infrared spectroscopy FTIR spectroscopy. This technique is capable of detecting the stretching vibrations of carbon-carbon double bonds involved in polymerization and thus it proved its feasibility to monitor the degree of conversion of orthodontic resin cement. Fourier-transform infrared spectroscopy FTIR spectroscopy is a widely used technique for investigating materials in the gaseous, liquid or solid phase. It is based on the interaction between electromagnetic radiation and natural vibrations of the chemical bonds among atoms that compose the matter. FTIR which can detect the stretching vibrations of carbon-carbon double bonds involved in polymerization. The method typically utilizes the height ratio of the peaks corresponding to aliphatic ($1,637$ $cm^{-1}$) and aromatic ($1,715$ $cm^{-1}$) double bonds to determine the DC. FTIR-ATR is more versatile than transmission FTIR because it eliminates the need of KBr (NaCl) plates, sectioning of thin wafers, or cure of the material in a thin film form. This simplifies sample preparation and, more importantly, allows the resin to be cured under conditions closer to clinical cases. FTIR-ATR also has an edge on evaluating the degree of conversion over hardness test as it was reported previously.

Objects bound to teeth with dental cement or dental resin. These include, but are not limited to any type of orthodontic bracket, fixed orthodontic appliance, dental fixed appliance made of any material, or dental prosthetic manufactured from any material which are bound to a tooth or teeth with a dental cement or dental resin. Examples include orthodontic materials or devices, cemented laminates, veneers, fixed dental crowns, and fixed dental bridges.

EMBODIMENTS

Although specific embodiments have been illustrated and described herein, any arrangement calculated to achieve the same purpose may be substituted for the specific embodiments shown. This disclosure is intended to cover any and all adaptations or variations of various embodiments. Combinations of the embodiments described herein and other embodiments not specifically described herein will be apparent to those of skill in the art upon reviewing the above description.

One embodiment of the invention is directed to a composition having a pH ranging from pH 6.0 to 8.0 comprising eugenol, at least one crosslinked polymer of acrylic acid or at least one other gelling agent, and at least one polysorbate or at least one other surfactant; wherein the amount of eugenol is sufficient to reduce the Vickers hardness of a cured or hardened orthodontic bonding adhesive cement or resin to a value of 70 or less after contacting it for at least 10 mins and/or is sufficient to reduce debonding force needed to remove a metal bracket from an enamel surface of a tooth. In other embodiments, one or more of the ingredients described above may be replaced with at least one functional equivalent. In some embodiments the pH may range from 5.0, 5.5, 6.0, 6.5, 7.0, 7.5 or 8.0. Saliva usually has a pH ranging from 6.2 to 7.6 and pH of a composition of the invention may be matched to that of the oral pH or to be 0.25, 0.5, 0.75, or 1.0 pH units below or above it.

In some embodiments the composition of the invention will contain eugenol, such as eugenol in the form of clove oil or synthetic eugenol in an amount ranging from about 0.5 to 10 wt %. This range includes all subranges and intermediate values such as about 0.5, 0.75, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5 and 10. In other embodiments, the composition can contain an amount of eugenol within the above-mentioned range or a lower or higher of eugenol (e.g., 0.10, 0.25, 0.5, 1.0, 5.0, 10.0, 15, 20, 30, 40, 50, 60, 70, 80, 90 or ≤100 wt % eugenol) provided that the selected amount is sufficient to reduce the Vickers hardness of a cured or hardened orthodontic bonding adhesive cement or resin to a value of 100, 90, 80, 70, 60, 50, 40, 30, 20 or less after contacting it for at least 10 mins and/or is sufficient to reduce debonding force needed to remove a metal bracket from an enamel surface of a tooth compared to an otherwise identical composition that does not contain eugenol or that contains peppermint oil or another volatile compound instead of eugenol. The composition of the invention may be in solid, particulate, semi-solid, semi-liquid, liquid, droplet, aerosol, vaporous or gaseous form.

In some embodiments the eugenol-containing composition will contain about 0.5 to 10 wt % of one or more types of crosslinked polymers of acrylic acid or Carbopol 934 or 940 and/or at least one hydroxy propyl methyl cellulose, polaxamer, or carboxy methyl cellulose sodium polymer. This range includes all subranges and intermediate values such as about 0.5, 1.0, 1.5, 2,0, 2.5, 3.0, 3.5, 4.0, 4.5, 5.0, 5.5, 6.0, 6.5, 7.0, 7.5, 8.0, 8.5, 9.0, 9.5 and 10. However, a greater or lesser amount of these gelling agents is incorporated depending on the degree of viscosity desired.

In other embodiments the composition will contain at least one surfactant such as polysorbate including polysorbate 20 or polysorbate 80, a cremophore (e.g., Cremophor®, Kolliphore®) produced by reacting ethylene oxide with each mole of castor oil such as the composition described by CAS number 61791-12-6, or other non-toxic surfactant. Preferably, a surfactant is incorporated in an amount ranging from about 1 to 40 wt % of the total weight of the composition. This range includes all subranges and intermediate values such as about 1.0, 1.5, 2,0, 2.5, 3.0, 3.5, 4.0, 4.5, 5.0, 5.5, 6.0, 6.5, 7.0, 7.5, 8.0, 8.5, 9.0, 9.5, 10, 15, 20, 25, 30, 35 and 40.

In other embodiments, the composition will contain a co-surfactant such as polyethylene glycol, propylene glycol, or glycerol, preferably in an amount ranging from 2 to 30 wt % based on the total weight of the composition.

In some embodiments, the composition will also contain a preservative such as a paraben (para-hydroxybenzoate which may be substituted with a $C_1$-$C_6$ or other alkyl group, such as methyl-paraben, propy-1-paraben, or butyl-paraben) in an amount sufficient to inhibit microbial growth, prevent oxidation, or otherwise extend the useful life of the composition. Preferably, the content of the preservative ranges from 0.01 to 0.45 wt % of the weight of the composition. This range includes all subranges and intermediate values such as about 0.01, 0.05, 0.1, 0.15, 0.20, 0.25, 0.30, 0.35, 0.40 and 0.45.

In some preferred embodiments a composition of the invention includes 5-15 wt % clove oil, 20-30 wt % polysorbate 20 (TWEEN 20®), 10-15 wt % propylene glycol, 1-3 wt % crosslinked polyacrylate polymer and water.

The viscosity and eugenol content of a composition according to the invention may vary depending in part on the site, oral pH, age or chemical composition of a cement or resin, and intended length of application time. In some embodiments the viscosity will range from about 1,000 to 5,000 cP in others the viscosity will exceed 5,000 cP. This range includes all subranges and intermediate values such as 1,000, 1,250, 1,500, 1,750, 2,000, 2,500, 3,000, 3,500, 4,000, 4,500, and 5,000.

Figure 4:
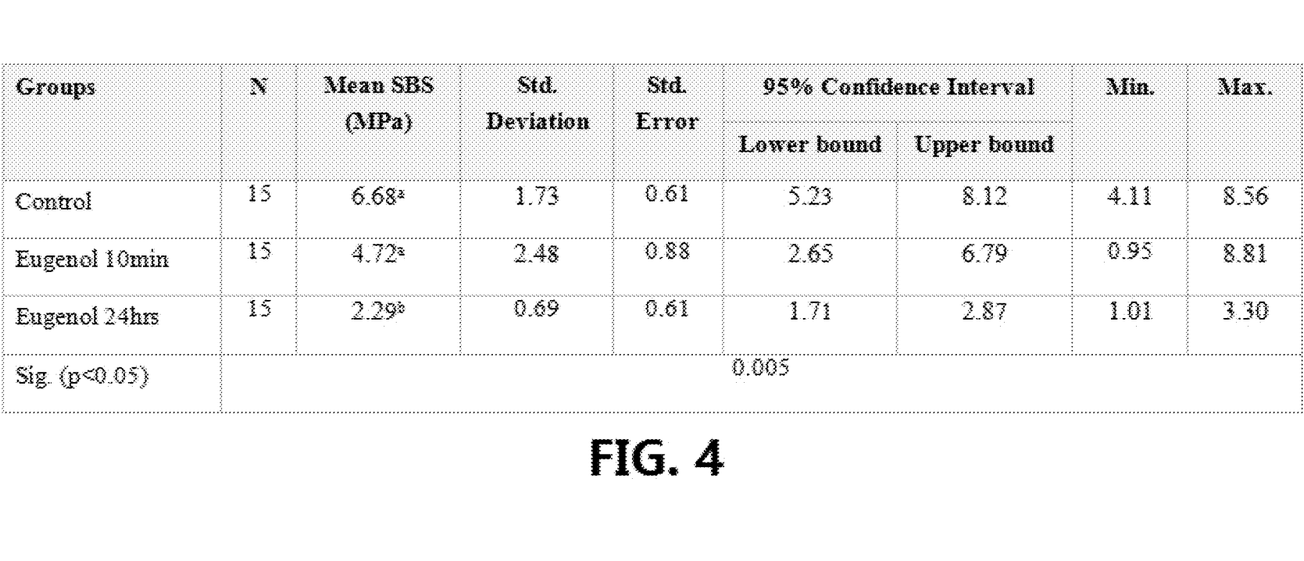
FIG. 4 depicts Table 1. This table shows descriptive statistics for the shear debonding force (MPa) for three assessed groups. Using One-way ANOVA & Post Hoc Tukey's test; means with different letters indicates a significant difference at $p<0.05$.

Another embodiment of the invention is directed to a method for removing a dental adhesive or cement from a tooth or other dental substrate, dental appliance, or prosthetic comprising contacting the dental adhesive or cement with eugenol, isoeugenol, methyl-eugenol or an isomer thereof. Preferably, the composition used in this method will contain eugenol, but other eugenol-like compounds may also be used or combined with eugenol. In this method the eugenol-containing composition is applied to a dental adhesive or cement bonds an orthodontic bracket to an enamel surface of a tooth with the eugenol preferably contained in a gel, such as a gel including eugenol, at least one surfactant, and at least one gelling agent. The eugenol-containing composition may also be applied as a varnish or as an adhesive coating that sticks to the dental adhesive or cement. In some embodiments, this method will reduce the Vickers hardness of the dental adhesive or cement below 90, 80, 70, 60, 50, 40, 30, 20 or 10. In some embodiments this method will reduce the to reduce debonding force needed to remove a metal bracket from an enamel surface of a tooth by 5, 10, 15, 20, 30, 40, 50, 60, 70, 80, 90, 100% or more compared to an otherwise identical composition not containing the eugenol or containing an otherwise identical composition containing a different active ingredient, such as peppermint oil. For example, sheer debonding force may be reduced from more than 6 mPA to less than 5, 4.5, 4, 3.5, 3, or 2.5 mPA as shown by FIG. 4. Dental cement or resin may also be debonded using the method of the invention from other dental substrates, such as from dentin, enamel, metal, ceramic, porcelain, and zirconia substrates.

In another embodiment, the method according to the invention will produce debonded teeth having an adhesive remnants index (ARI) scores of 0, 1, 2 or 3 and comprise removing these remnants. ARI scores may vary depending on type of cement or resin applied, content of eugenol in a debonding composition, and amount of time cement or resin is contacted with a debonding composition. Debonded teeth may be characterized by MU scores of 0, 1, 2, 3 and/or 4 for at least 0, 12.5, 25, 50, 62.5, 75, or 100% of teeth or intermediate values within this range based on the number of teeth debonded.

In some embodiments, the method will involve brushing, buffing, polishing, washing or etching or otherwise cleaning a contact surface of the dental cement or resin to remove microbial or chemical coatings prior to contacting it with the eugenol in the form of a gel. In other embodiments, residual dental cement or resin is removed after debonding of the dental bracket, appliance, or prosthetic. Such removal is generally easier and safer because eugenol has softened the residue material permitting it to be more safely removed.

Another embodiment of the invention represents a kit containing a eugenol-containing composition as disclosed herein, a tray suitable for retaining the composition and contacting the composition with at least one dental fixture bonded with a dental cement or resin to teeth, and, optionally, packaging materials and/or instructions for use. This kit may contain a tray that is customized or cast to fit over a subject's teeth and brackets or other dental fixtures.

Another embodiment is directed to a method for debonding metal brackets, a dental appliance or dental prosthetic by filling a tray with a composition comprising eugenol, or a eugenol gel or other eugenol-containing composition; fitting the tray over teeth that are bonded to metal brackets, a dental appliance, or a dental prosthetic for a time sufficient to reduce Vickers hardness of a dental cement or resin binding the metal brackets, dental appliance or dental prosthetic to the teeth, and debonding the metal brackets, a dental appliance, or a dental prosthetic from the teeth.

In another embodiment, the invention is directed to curable or hardenable dental cement or resin that is "preloaded" with an amount of eugenol, isoeugenol, methyl-eugenol or an isomer thereof that does not negatively affect is ability to bond dental brackets, appliances or prosthetics to dental surfaces, but that is easier or faster to remove by contacting it debonding with eugenol, such as a eugenol emulgel to increase a threshold amount of eugenol in the cured dental cement or resin to one that softens it. This curable or hardenable dental cement or resin can comprise a conventional dental cement or resin such as those known in the art or described herein to which eugenol is added. Eugenol is added in an amount that does not significantly reduce the ability of the cement or resin to bond metal braces, brackets or dental fixtures to teeth, but that facilitates removal of the cement or resin with a eugenol-containing composition of the invention. This cement or resin may thus be used for bonding and then in combination with a eugenol-containing composition of the invention to facilitate fast and safe debonding of dental brackets and other fixtures from enameled surfaces of teeth. In one embodiment components for forming or applying a cured dental cement or resin containing eugenol for use in dental bonding, and those of an emulgel or components for making it for later use in debonding are combined in a single kit. In some embodiments one or more of eugenol, isoeugenol, methyl-eugenol or an isomer thereof are incorporated into the dental cement or resin.

EXAMPLES

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. The following examples illustrate various aspects of the present invention. They are not to be construed to limit the claims in any manner whatsoever.

The inventors assessed the effect of eugenol on the orthodontic adhesive material and the debonding behavior of metal brackets with an objective of developing a clinically applicable method for using eugenol compositions debond orthodontic brackets. As the bracket-adhesive interface in metal brackets is very thin, eugenol was prepared in the form of gel to ensure its retention around the bracket. The eugenol-containing gel was applied for an in-clinic applicable period of 10 min and an out-clinic period 24 hr.

Example 1

Eugenol Emulgel Preparation

An emulgel was prepared from 10 wt % clove oil, 27 wt % polysorbate 20 (TWEEN 20®), 13 wt % propylene glycol, 1.5 wt % crosslinked polyacrylate polymer and 48.5 wt % water. The crosslinked polyacrylate polymer was CARBOPOL 934® which is incorporated by reference to http://_www.surfachem.com/carbopol-934, last accessed Jul. 23, 2017.

A solubilized system gel was prepared by first mixing propylene glycol with clove oil to produce an oily phase. An aqueous phase was then prepared by incorporation of TWEEN 20® with a portion of deionized water. For the preparation of gelling phase, CARBOPOL 934® was dispersed using an IKA UTRATURAX T10® (Switzerland) homogenizer and neutralized to a pH 6.0-6.5 with 0.5 M sodium hydroxide. The aqueous phase was added drop wise to the oily phase while mixing until a clear homogenous solubilized system formed. The gelling phase was then added slowly to solubilized system until a homogenous clear/opalescent gel formed.

Example 2

Application of the Eugenol Emulgel on Bonded Dental Brackets

Bonded brackets to the teeth were fixed onto a dental model (Nissin-Dental, Tokyo, Japan) using high fusing impression compound. Alginate impressions were made for all models having the teeth with bonded brackets attached to it. Casts were prepared and each tooth bearing bracket on the dental cast was blocked with paraffin wax to obtain space for eugenol-containing emulgel delivery. A polypropylene sheet (Easy Vac-Gasket, 3A MEDES, Korea) was vacuum-adapted to each cast with a vacuum-forming machine (Henry Schein, Henry Schein Inc., NY, USA). From the vacuum adapted sheet, individual trays were made to fit onto the tooth surfaces to cover the complete arch of the teeth on the model and were trimmed to be approximately 1 mm above the gingival margin. The eugenol emulgel was applied to the brackets bonded to the teeth using the customized trays and then the whole model was placed in a container having distilled and placed in incubator for 24 hours.

Micro-hardness assessment. One hundred and twenty Transbond composite resin and Transbond primer discs (3M, St. Paul, Minn., USA) were prepared by filling a plastic mold (10 mm inner diameter×2 mm depth). The exposed surfaces were then covered by Mylar matrix strips and light cured using a light curing unit (Luxor lamp, ICI Plc, Macclesfield, Cheshire, UK). All specimens were stored in distilled water at 37° C. for 1 day to ensure complete polymerization of the resin materials.

The discs were divided into six groups, three groups for the Transbond composite and three groups for the Transbond primer (n=20 each) as follows; control, eugenol 10 min application and eugenol 24 hr application.

In the two eugenol groups, eugenol-containing emulgel was applied to the surface of the discs using a brush and left for 10 min and 24 hr before being washed away with water emitted from a triple syringe. All discs were then subjected to ten indentations, with a load of 200 g for 20 sec using a micro-hardness tester (HMV-2000 Shimadzu, Japan) and the Vickers hardness values were recorded.

Bond strength assessment. Based on 80% power of test, 45 sound extracted premolars, with no obvious enamel cracks were collected and stored in distilled water.

Teeth were then cleaned, polished with non-fluoridated pumice and rubber prophylactic cups for 15 sec, rinsed with water spray for 10 sec and then dried with oil-free compressed air for 10 sec.

The buccal surfaces were etched with 37% phosphoric acid solution for 30 sec according to the manufacturer's instructions, rinsed with water spray for 20 sec and then dried with oil-free compressed air for 20 sec.

All teeth were bonded with metal brackets under constant load using Transbond XT light cured composite resin (3M, St. Paul, Minn., USA), and stored in distilled water at 37° C. in an incubator for one week to ensure complete polymerization of the adhesive resin.

The sample was then randomly divided into three groups (n=15 each): control, eugenol 10 min application, and eugenol 24 hr application.

All teeth were then debonded with a narrow blade debonding plier (AEZ Debonding Orthodontic Plier, Ormco Corporation, USA) mounted on an Instron Universal Testing machine according to the modified method followed by Bishara et al., Horiuchi et al., and Hama et al. Bishara S E, "Comparisons of the effectiveness of pliers with narrow and wide blades in debonding ceramic brackets". Am J Orthod Dentofacial Orthop 1993;103:253-257; Bishara, et al., "Debonding forces applied to ceramic brackets simulating clinical conditions", Angle Orthod. 1994;64:277-282; Horiuchi S, Kaneko K, Mori H, Kawakami E, Tsukahara T, Yamamoto K, et al. "Enamel bonding of self-etching and phosphoric acid-etching orthodontic adhesives in simulated clinical conditions: debonding force and enamel surface". Dent Mater J 2009; 28:419-425; and Hama T, Namura Y, Nishio Y, Yoneyama T, Shimizu N. Effect of orthodontic adhesive thickness on force required by debonding pliers. J Oral Sci 2014; 56:185-190, each of which is incorporated herein by reference in their entirety. Such method was chosen because it simulates the clinical situation. The stainless steel blades of the pliers were placed at the bracket-adhesive interface, and a squeezing action at a crosshead speed of 0.5 mm/min was applied to the plier at room temperature until bond failure occurred and the debonding strength was recorded.

Figure 1A:
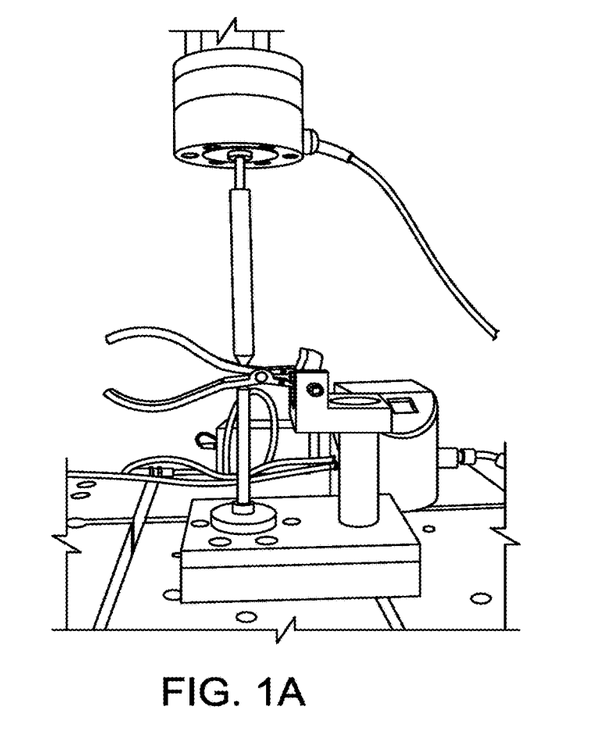
FIG. 1A shows the design of the AEZ debonding plier mounted on the Instron machine.
Figure 1B:
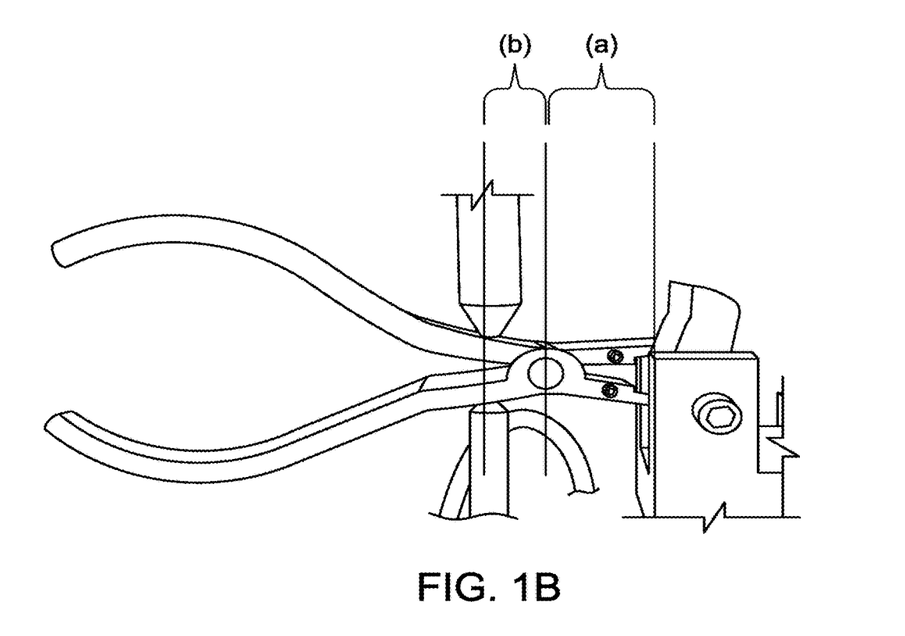
FIG. 1B shows how the distances (a) and (b) used to calculate the actual debonding force are measured.

The debonding force by the Instron was applied at a predetermined constant distance on the arms of the plier. Thus, the actual debonding strength was calculated using the following formula:

The actual debonding strength=measured strength (by the Instron machine)×(b/a)

Where (a) is the distance between the blades of the plier at the bracket-adhesive interface and the fulcrum of the plier, while (b) is the distance from where the force is applied on the plier's arms by the Instron machine to the fulcrum of the plier (FIG. 1). The conversion factor (b/a) used in this study was calculated to be 0.55.

All teeth were examined under a stereomicroscope at 10×, and 20× magnification for the residual adhesives remaining on the buccal enamel surfaces.

The amount of adhesive remnant was then scored using the modified Adhesive Remnant Index (ART) as follows:
Score 0: no retained resin (0%).
Score 1: ≤50% retained resin on the enamel surface (>0%-≤50%).
Score 2: >50% retained resin on the enamel surface (>50%-<100%).
Score 3: all resin retained on the enamel surface with bracket imprint (100%).

Additional details of ARI scoring are incorporated by reference to Årtun J, Bergland S. Clinical trials with crystal growth conditioning as an alternative to acid-etch enamel pretreatment. Am J Orthod1984; 85:333-340.

FTIR/ATR analysis. Fourier-transform infrared (FTIR) spectrometer (Thermo Nicolet™ iS™ 5 FT-IR Spectrometer, Thermo Electron Corporation, MA, USA) was performed with the attenuated total reflectance (ATR) accessory and a plate of zinc selenite crystal at 45°. All measurements were obtained under the following conditions: resolution of 4 cm$^{-1}$ and four internal scans per reading. For each cured resin, the same non-cured resin served as the control. After obtaining the readings for the non-cured resin; curing of the examined two types of resins was carried out according to manufacturer instructions, holding the light curing unit at constant distance of 2 mm from the examined resins. Each of the cured resins were numbered and randomly assigned into three groups; Control (stored in distilled water 24 hours), Eugenol 10 min (application of eugenol for 10 mins; washed and then stored in distilled water for 24 hours), and Eugenol 24 hr (application of eugenol for 24 hours then washing by distilled water).

Before the first reading and between each new set of measurements of the non-cured resin (monomer) and cured resin (polymer), a baseline spectrum background was obtained with all the artefacts that would be used before curing the Transbond XT. The purpose of this first measurement was to determine the spectra of the artifacts used in the measurements, which would be deducted by the equipment in the subsequent monomer and polymer measurements of each specimen as described by Kawabata R, Hayakawa T, Kasai K. "Modification of 4-META/MMA-TBB resin for safe debonding of orthodontic brackets—influence of the addition of degradable additives or fluoride compound". Dent Mater J 2006;25:524-532, incorporated herein by reference in its entirety.

The light was applied on the opposite side of the infrared reading beam scan. Between each set of monomer/polymer spectra, the crystal plate of the ATR accessory was cleaned with absorbent paper and acetone and then dried with air blower, so that there would be no residues to prejudice the new set of monomer/polymer spectrum measurements.

The measured spectra for all systems contained the following major peaks: stretching vibrations of aliphatic C=C at 1,638.6 cm$^{-1}$, of C=O at 1730 cm$^{-1}$, of C—H groups at -2,900 cm$^{-1}$ and of O-H at N 3,500 cm$^{-1}$. To understand the effect of Eugenol on the primer and the composite resin, ratios of the absorbance intensities (AI) of these peaks to that of the aromatic C=C at 1609.4 cm-1 were calculated. Aromatic C=C bonds are considered stable in resins. The C=C bonds of benzene are stable, probably as a result of delocalized electrons in which resonance (or delocalization) energy is required to hold them in place. Each set of scraping samples from the specimen was analyzed two times. A mean and standard deviation of ten analyses for each group (five specimens) were computed and a statistical analysis of AI was performed.

Statistical Analysis. Data were analyzed using descriptive statistics to report the means and standard deviations for the microhardness values, shear bond strength (MPa), and the ART scores for the three groups. Inferential statistics for mean comparison in microhardness and shear bond strength values was conducted using One-way ANOVA and Tukey's Post Hoc test. Kruskal Wallis test was conducted for ARI scores comparison between the three groups. All data were analyzed using SPSS statistical analysis software program (Version 16, SPSS Inc., Chicago, USA). Significance level was set at (p<0.05).

Figure 2A:
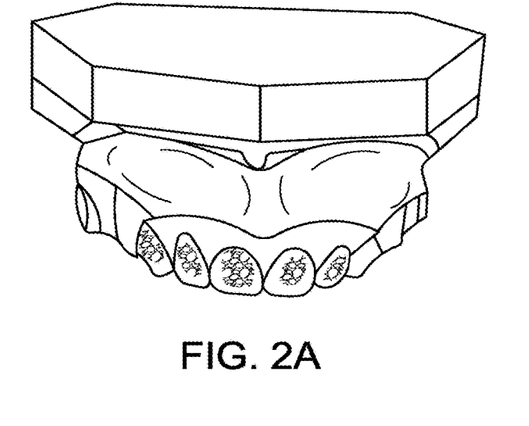
FIGS. 2A, 2B and 2C depict debonding equipment. A model for orthodontically treated patient ready for debonding is shown by FIG. 2A. A flexible tray constructed on the model allowing space for the emulgel application and sealing off the effect of emulgel from the gingiva is shown by FIG. 2B. The flexible tray filled with the emulgel and ready to be used intraorally is shown by FIG. 2C. Trays and eugenol-containing emulgel may be distributed to orthodontic subjects prior to debonding procedures, for example, for use 4, 6, 8, 10, 12, 16, 20 or 24 hours before a procedure.
Figure 2B:
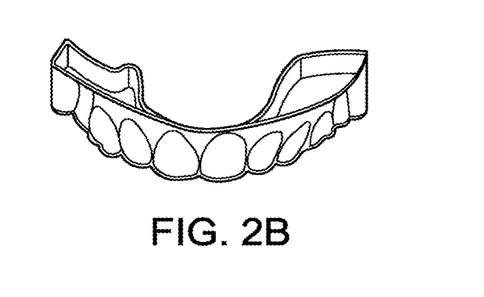
Figure 2C:
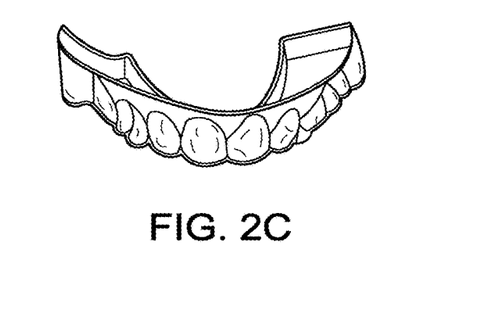
Figure 3:
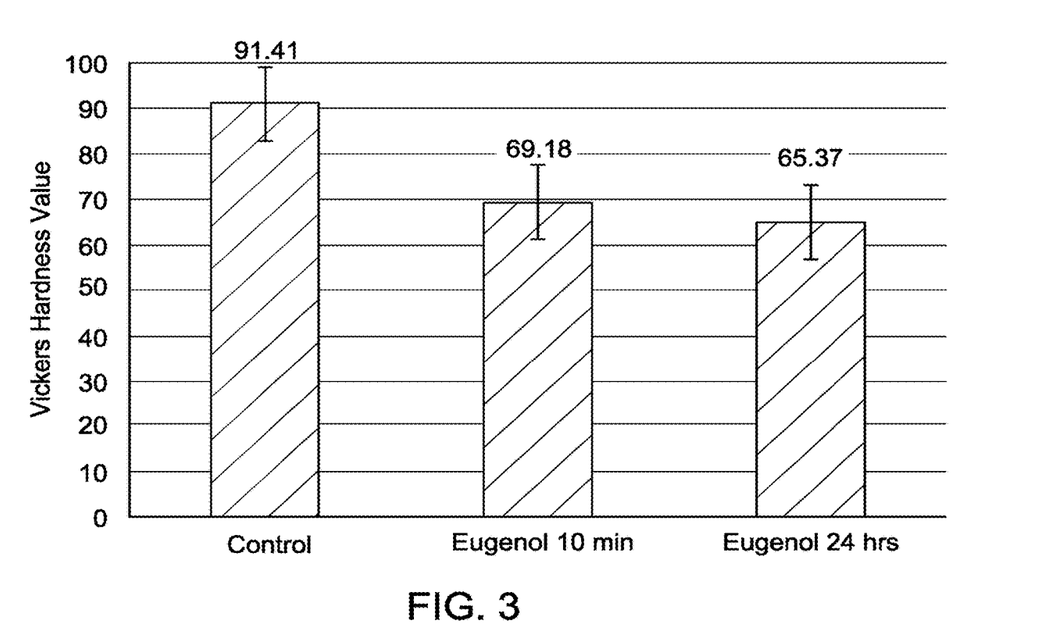
FIG. 3 shows the mean and standard deviations of the Vickers microhardness values for the two groups assessed. Error bars indicate a standard deviation. A significant difference was found at $p<0.05$.

Microhardness. The mean Vickers hardness value for the control group (91.41+/−6.95) was significantly higher than the two eugenol groups; 10 min application (69.18+/−6.95) and 24 hr application (65.37+/−8.66) at p<0.05 (FIG. 2).

Debonding strength. The eugenal 24 hr application showed significantly lower mean shear bond strength (2.29+/−0.69 MPa) than the other two groups: control (6.68+/−1.73 MPa) and eugenol 10 min group (4.72+/−2.48 MPa) at p<0.05 (FIG. 4, Table 1).

Figure 5:
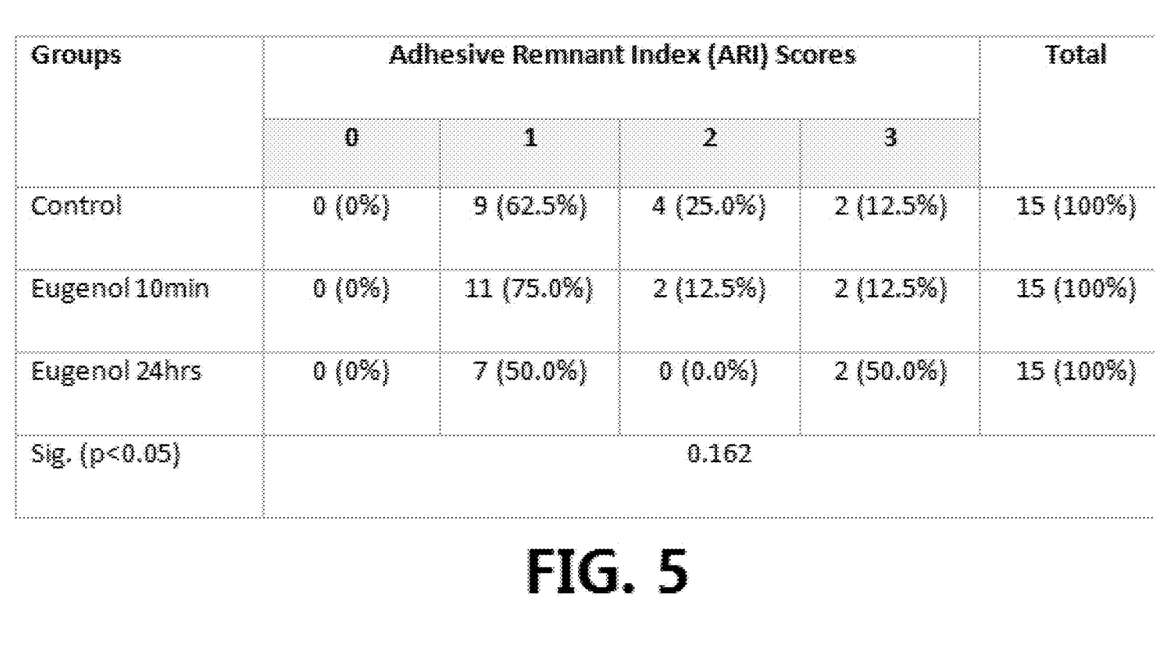

Adhesive remnants. Kruskal Wallis test revealed no significant difference in the adhesive remnant scores after debonding between the three groups (p>0.05). More than 50% of the sample in all groups had ARI score 1 (≤50% retained resin on the enamel surface). Concomitantly, none of the sample had ARI score (0) where no adhesive remained after debonding (FIG. 5, Table 2).

FTIR/ATR results. Ratios of Absorbance intensities for the aliphatic C═C ($1,638.6$ $cm^{-1}$) and the C═O at $1730$ $cm^{-1}$ to that of the aromatic C═C peak ($1,609$ $cm^{-1}$) decreased significantly upon application of the emulgel on the XT resin surface and the XT primer for 24 hr at p<0.05. There was no significant effect p<0.05 on the aforementioned ratios when the emulgel was applied on the XT resin surface and the XT primer for 10 minutes.

Comparative Advantage of Debonding Method of the Invention. The effects of other chemical solvents, such as peppermint oil on the debonding of orthodontic brackets were described by Larmour C J, Chadwick R G. "Effects of a commercial orthodontic debonding agent upon the surface microhardness of two orthodontic bonding resins". J Dent 1995;23:37-3, incorporated herein by reference in its entirety.

Larmour, in his two studies, assessed the effectiveness of a viscous gel containing a derivative of peppermint oil that was marketed in the 90's as a post-debonding agent (P-de-A, Oradent Ltd, Eton, Berks. UK) for debonding ceramic brackets. They found that a 60 sec application of peppermint gel can have a significant positive effect on the debonding strength and the failure of bond at the adhesive/enamel interface when debonding ceramic brackets.

On the other hand, Larmour & Chadwick reported no significant effect of such product on the microhardness of Transbond light cured adhesive material.

In comparison to these studies, the inventors show a significant reduction in the microhardness of the Transbond XT light cured composite resin after both 10 min as well as 24 hr of eugenol application and that debonding strength was significantly reduced after 24 hr of eugenol application.

The amount of adhesive remnant was not significantly changed with the use of eugenol. It can also be noted that the mean hardness value reported in this study was in the range of (65.37-69.18) while the mean value after 180 sec of peppermint oil application was (112.02+/−13.87). These results indicate that eugenol seems to reduce the microhardness significantly more than peppermint oil.

Eugenol, in the current study, is found to have an effect on debonding metal brackets after 24 hr. However, a 10 min application of eugenol, as designed in this study, did not reduce the debonding strength and the adhesive remaining after debonding metal brackets to a level that is competitive to the control.

On the other hand, the microhardness results for the primer and the composite showed decreased values after the 10 min and 24 hr of eugenol application; the obtained results may be explained as follows; Eugenol emulgel exerted an immediate softening effect on the XT resin cement and on the XT polymerized primer, however, these softening effects were not enough to weaken the bond strength of the metallic brackets bonded to the enamel surfaces. The eugenol softening effects on the resin cement and on the primer were accentuated after 24 hr which were manifested as a significant decrease in bond strength after 24 hr of eugenol application. The aforementioned hypothesis was supported by the FTIR results which showed that the 10 min eugenol application did not show detectable chemical changes for the 10 min eugenol group while, a significant changes for FTIR peaks were observed after the 24 hr eugenol application.

As disclosed here the eugenol-containing compositions of the invention significantly reduced the microhardness of adhesive orthodontic bonding resins and significantly decrease the debonding strength of metal brackets, thus providing an effective and safer way to remove dental apparatus from teeth.

Terminology. Terminology used herein is for the purpose of describing particular embodiments only and is not intended to be limiting of the invention.

The headings (such as "Background" and "Summary") and sub-headings used herein are intended only for general organization of topics within the present invention, and are not intended to limit the disclosure of the present invention or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

Links are disabled by insertion of a space or underlined space before "www" and may be reactivated by removal of the space.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all sub-ranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it is also envisioned that Parameter X may have other ranges of values including 1-9, 2-9, 3-8, 1-8, 1-3, 1-2, 2-10, 2.5-7.8, 2-8, 2-3, 3-10, and 3-9, as mere examples.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Spatially relative terms, such as "under", "below", "lower", "over", "upper", "in front of" or "behind" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. A method for removing a metal bracket bound to a tooth or teeth via a dental resin, comprising:
   filling a tray with a composition comprising eugenol, at least one polysorbate surfactant and at least one cross-linked acrylic acid polymer gelling agent,
   fitting the tray the tooth or teeth to contact the dental resin with the gel for a time sufficient to reduce a Vickers hardness of the dental resin to a value of no more than 70, and
   removing the metal bracket from the tooth or teeth.

2. The method of claim 1, wherein the gel comprises eugenol in an amount ranging from 0.5 to 10 wt %, relative to a total weight of the gel.

3. The method of claim 1, wherein the gel comprises 0.5 to 10 wt % of the at least one gelling agent.

4. The method of claim 1, wherein the gel comprises 1 to 40 wt % of the at least one polysorbate surfactant.

5. The method of claim 1, wherein the gel further comprises 2 to 30 wt % of at least one of polyethylene glycol, propylene glycol, and glycerol.

6. The method of claim 1, wherein the gel has a viscosity ranging from 1,000 to 5,000 cP.

* * * * *